(12) United States Patent
Trapani

(10) Patent No.: US 10,226,541 B2
(45) Date of Patent: Mar. 12, 2019

(54) ROOM STERILIZATION METHOD AND SYSTEM

(71) Applicant: Samuel Richard Trapani, Rochester, NY (US)

(72) Inventor: Samuel Richard Trapani, Rochester, NY (US)

( * ) Notice: Subject to any disclaimer, the term of this patent is extended or adjusted under 35 U.S.C. 154(b) by 347 days.

(21) Appl. No.: 15/169,164

(22) Filed: May 31, 2016

(65) Prior Publication Data

US 2016/0271282 A1 Sep. 22, 2016

Related U.S. Application Data

(60) Continuation of application No. 14/263,774, filed on Apr. 28, 2014, now Pat. No. 10,010,633, and a division of application No. 13/964,874, filed on Aug. 12, 2013, now Pat. No. 9,345,798, said application No. 14/263,774 is a continuation-in-part of application No. 13/964,874, filed on Aug. 12, 2013, now Pat. No. 9,345,798, and a continuation-in-part of application No. 13/446,563, filed on Apr. 13, 2012.

(60) Provisional application No. 61/475,722, filed on Apr. 15, 2011.

(51) Int. Cl.

| *A61L 2/10* | (2006.01) |
|---|---|
| *A61L 2/24* | (2006.01) |
| *A61L 2/20* | (2006.01) |
| *A61L 9/015* | (2006.01) |
| *A61L 9/20* | (2006.01) |
| *G01J 1/42* | (2006.01) |
| *G01J 1/02* | (2006.01) |

(52) U.S. Cl.
CPC .............. *A61L 2/10* (2013.01); *A61L 2/202* (2013.01); *A61L 2/208* (2013.01); *A61L 2/24* (2013.01); *A61L 9/015* (2013.01); *A61L 9/20* (2013.01); *A61L 2202/11* (2013.01); *A61L 2202/14* (2013.01); *A61L 2202/16* (2013.01); *A61L 2202/25* (2013.01); *G01J 1/429* (2013.01); *G01J 2001/0276* (2013.01)

(58) Field of Classification Search
CPC ...................................................... A61L 2/10
See application file for complete search history.

(56) References Cited

U.S. PATENT DOCUMENTS

| 6,911,177 B2 * | 6/2005 | Deal ......................... A61L 2/10 |
|---|---|---|
| | | 250/455.11 |
| 2012/0305787 A1 * | 12/2012 | Henson ..................... A61L 2/10 |
| | | 250/372 |

\* cited by examiner

Primary Examiner — Donald R Spamer
(74) Attorney, Agent, or Firm — Hulsey P.C.

(57) ABSTRACT

A sterilization system consisting of a mobile emitter, a sensing subsystem and a data logging subsystem is described. The emitter has one or more UV emitting lamps or devices. The sensing system comprises at least one remote UV sensor and at least one door sensor. The door sensor comprises a safety shut off door detector and may contain an emergency stop detector and arming detector to protect people from being exposed to UV energy. The system has a remote control for starting, stopping and setting system parameters which include but are not limited to: treatment time, dosage, room size, room number, unit number, floor, facility name, operator name, operator identification number, password, default dosage values, dosage, and patient identification number. The number of treatments per unit of time can be maximized because of the use of incident light measurement.

6 Claims, 5 Drawing Sheets

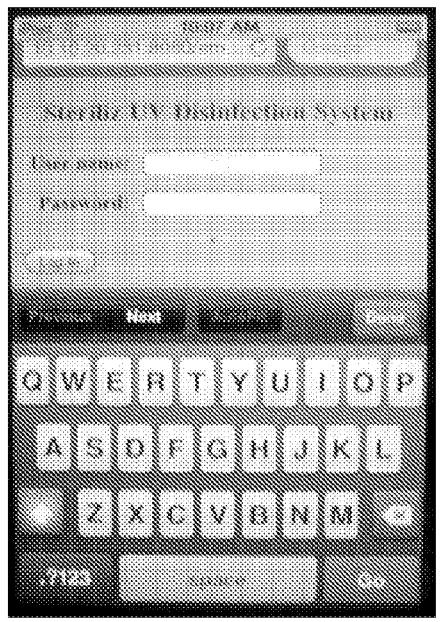
FIG. 3 (SCREENSHOT)
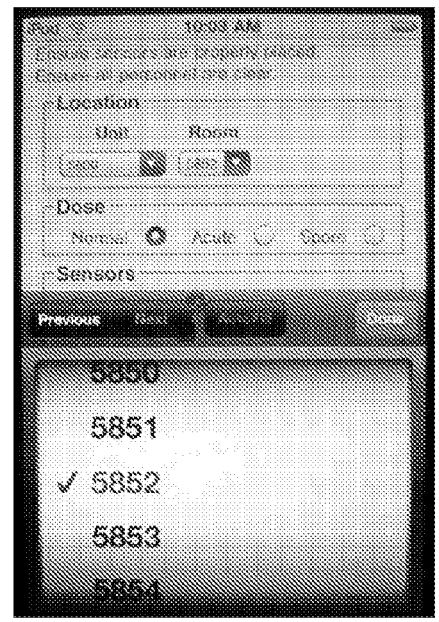
FIG. 4 (SCREENSHOT)
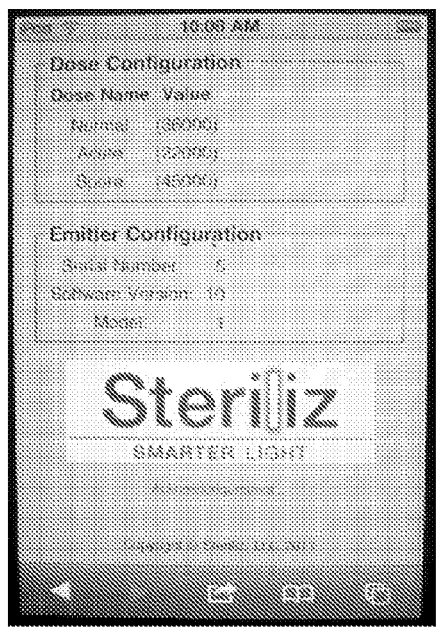
FIG. 5 (SCREENSHOT)
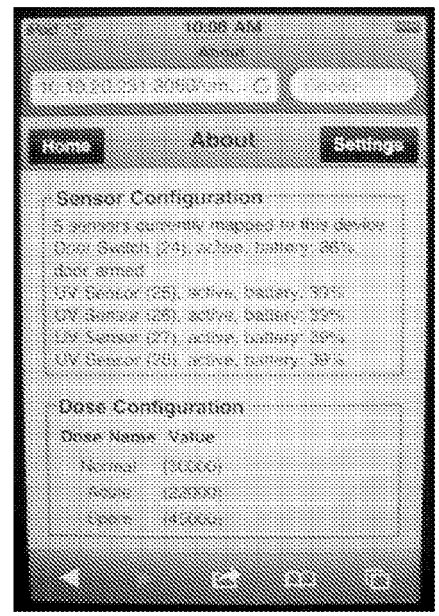
FIG. 6 (SCREENSHOT)

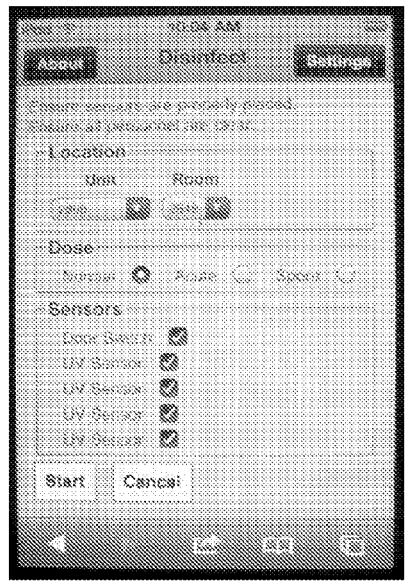
FIG. 7 (SCREENSHOT)
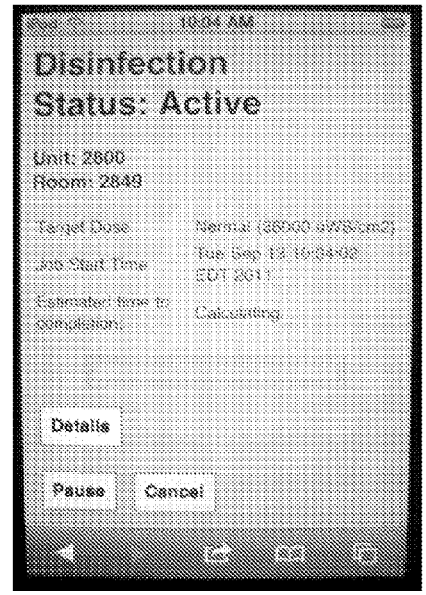
FIG. 8 (SCREENSHOT)
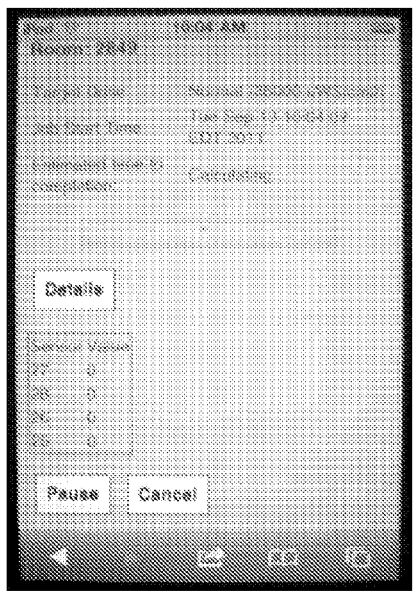
FIG. 9 (SCREENSHOT)
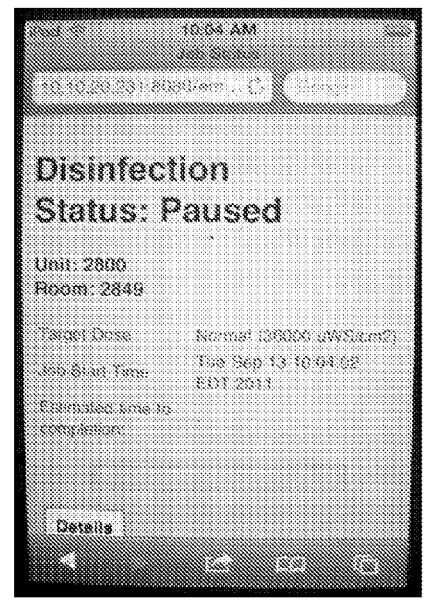
FIG. 10 (SCREENSHOT)

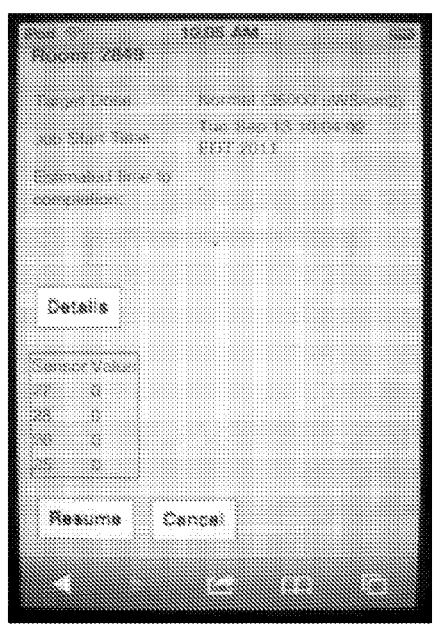
FIG. 11 (SCREENSHOT)
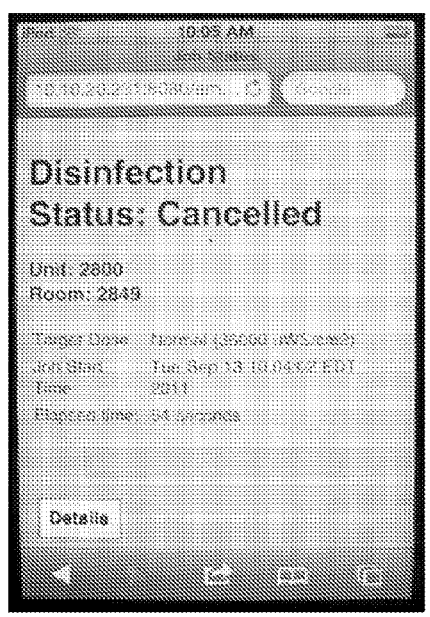
FIG. 12 (SCREENSHOT)

ROOM STERILIZATION METHOD AND SYSTEM

CROSS-REFERENCE TO RELATED APPLICATIONS

This application claims priority to U.S. Provisional Patent Application Ser. No. 61/475,722 filed Apr. 15, 2011, U.S. Non-Provisional patent application Ser. No. 13/446,563 filed Apr. 13, 2012, U.S. Non-Provisional patent application Ser. No. 13/964,874 filed Aug. 12, 2013 and U.S. Non-Provisional patent application Ser. No. 14/263,774 filed Apr. 28, 2014, which are hereby incorporated by reference in its entirety.

FIELD

The present disclosure relates to disinfection. More specifically, the present disclosure relates to disinfection of pathogens using ultraviolet (UV) light.

BACKGROUND

In the U.S. each year, more people die from hospital infections than from AIDS, breast cancer, and auto accidents combined. These infections are the fourth leading cause of death, with current annual estimates of 2,000,000 infections, 100,000 deaths, and added costs of $45 billion. Somewhere between 5-10% of all patients admitted to a hospital acquire an infection while in that hospital. Even with such extreme statistics, many industry experts consider the problem to be severely underestimated.

Currently, Clostridium difficile (C. diff) is one of the most problematic pathogens in the healthcare industry. It causes C. diff Infection (CDI) that sickens and kills humans. The Centers for Disease Control (CDC) states that C. diff spores are transferred to patients mainly via the hands of healthcare personnel who have touched a contaminated surface or item. They also say that to reduce the chance of spreading pathogens and subsequent disease, surfaces must be cleaned better.

Current cleaning methods such as a chemical disinfection are not working as a stand-alone practice, and additional measures need to be taken to reduce patient and healthcare professionals' risks. For more than 75 years UV light has been used to destroy pathogens in water supplies and HVAC systems. In recent years, products have been developed that utilize UV to disinfect surfaces and air.

In 1892, Professor Marshall Ward demonstrated that it was primarily the UV portion of the spectrum of light that had the ability to inactivate the DNA of pathogens thereby making them unable to multiply. Medical uses of UV light include sterilization of surfaces and air without the use of chemicals. There are many well documented studies that identify the specific amount (dosage) of UV light necessary to disinfect and sterilize surfaces and air.

One type of existing UV disinfection equipment uses either a manually operated switch or a timer to deliver UV light for a period of time. Another type of existing UV disinfection equipment is a system that measures reflected UV light, generally at the emitter, to control how much time the UV light is delivered. Both of these types of equipment are unable to definitively deliver a specific dosage to a surface or volume of air because there is no measurement being taken at the location of interest. This problem results in surfaces and air being over- or under-treated. In the case of over-treating, excess treatment time, which slows down the facility's operations thus adding to operating costs and reducing throughput, and excess exposure to room surfaces, which causes faster breakdown of the materials the surfaces are made from, may occur. In the case of under-treating, disinfection or sterilization is not assured, which may result in reduced efficacy and increased exposure to liability lawsuits.

SUMMARY

Therefore, it is an object of this disclosure to provide room disinfection and/or sterilization methods and apparatuses that satisfy the demands discussed above while improving on known shortcomings in the prior art.

The present disclosure discusses a mobile system which, when used properly, automatically delivers UV-C light to all surfaces within a treatment space, including hard-to-clean, high-touch surfaces such as keyboards, computers, and bed rails, yielding a significantly cleaner, safer environment.

When compared to other systems and techniques, this disclosure provides faster processing-time and critical data capture that clearly demonstrates treated areas have received the necessary dosage of UV-C light needed eradicate dangerous pathogens effectively. Another benefit of UV-C disinfection is that it leaves no harmful residue or vapors. The room is immediately available for occupancy.

The present disclosure comprises a room disinfection and sterilization system utilizing UV light to cause permanent and fatal injury to the pathogens that cause illness and death to humans. This system includes an emitter that produces UV light, one or more remote wired or wireless UV light sensors that measure the intensity of UV light incident upon them, one or more remote wired or wireless door sensor safety stop switch which causes the system to stop emitting UV light in the event the door being monitored is opened or if the safety stop switch is depressed, a wired or wireless remote control to operate the system, and a central computer with wireless local area network (WLAN, e.g. Wi-Fi, WICAD, bluetooth, 802.11, 802.15, 3G, 4G, CDMA, or other suitable technology) connect-ability to access the internet and provide local and remote logging of disinfection cycles or jobs. In some embodiments, the device of the present disclosure may include its own Wi-Fi access point, along with an Internet bridge (for example, a cellular modem). In some embodiments, the remote control may be a standard iPod or other PDA/smartphone/tablet/handheld device.

The present disclosure delivers lethal UVC light doses into all areas of complex environments, destroying viruses, spores, and drug-resistant bacteria, even in a room's shadowed areas. Its unique, next-generation remote sensors make this the only system that can measure how much UVC energy reaches every corner of a treatment space.

The present disclosure employs at least one remote sensor which definitively measures the precise dosage of UV light delivered to the location of interest. Data recording and reporting are necessary for tracking and analyzing infections acquired in facilities where disinfection occurs. A significant difference between the present disclosure and existing equipment and systems is the ability to store, retrieve, report and analyze such data. The present disclosure employs local storage of such data on the hard disk drive of its computer controller and remote data storage via up-linking to a remote internet host server for others to access.

These and other advantages of the disclosed subject matter, as well as additional novel features, will be apparent from the description provided herein. The intent of this summary is not to be a comprehensive description of the subject matter, but rather to provide a short overview of some of the subject matter's functionality. Other systems, methods, features and advantages here provided will become apparent to one with ordinary skill in the art upon examination of the following FIGURES and detailed description. It is intended that all such additional systems, methods, features and advantages included within this description, be within the scope of the claims.

BRIEF DESCRIPTIONS OF THE DRAWINGS

The features, nature, and advantages of the disclosed subject matter may become more apparent from the detailed description set forth below when taken in conjunction with the drawings in which like reference numerals indicate like features and wherein:

FIGS. 3-12 are screenshots of a remote operating device according to the present disclosure.

DETAILED DESCRIPTION

The present disclosure may be understood more readily by reference to the following detailed description, examples, drawings, and claims, and their previous and following description. However, before the present devices, systems, and/or methods are disclosed and described, it is to be understood that this disclosure is not limited to the specific devices, systems, and/or methods disclosed unless otherwise specified, as such can, of course, vary. It is also to be understood that the terminology used herein is for the purpose of describing particular aspects only and is not intended to be limiting.

As used in the specification and the appended claims, the singular forms "a," "an" and "the" include plural referents unless the context clearly dictates otherwise. Thus, for example, reference to a "sensor" can include two or more such analyzers unless the context indicates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Reference will now be made in detail to certain embodiments of the disclosure, examples of which are illustrated in the accompanying drawings. Wherever possible, the same reference numbers are used throughout the drawings to refer to the same or like parts.

Figure 1:
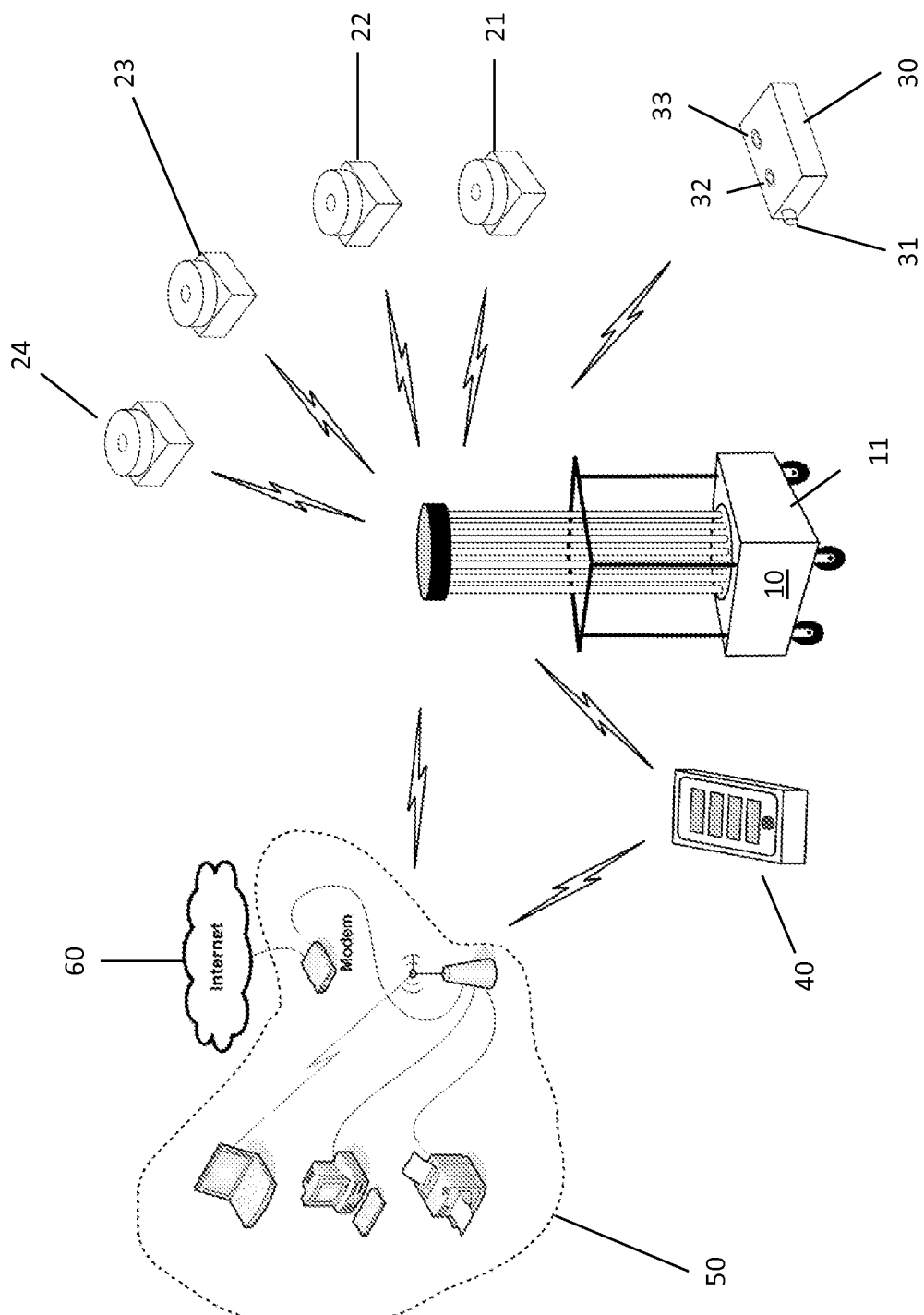
FIG. 1 is a perspective view of a disinfection system of the present disclosure.

Referring now to the figures in more detail, in FIG. 1, a sterilization system is shown consisting of emitter 10, a sensing system consisting of UV sensors 21-24, door sensor 30, remote control 40, optional wireless local area network (WLAN) 50, and optional Internet connection 60 for the optional WLAN.

In more detail, still referring to FIG. 1, we begin with a discussion of the emitter subsystem. This subsystem consists of an emitter 10 which is a mobile structure on wheels with a plurality of lamps that emit ultraviolet light when energized by their corresponding electronic ballast(s). Other forms of an emitter may be a mobile structure with another means for transporting without the use of integrated wheels, or a stationary structure. Neither of these are precluded. Also contained in this subsystem is central computer 11, which executes a software program that controls energization of the lamps and ballasts through the cycling of an interconnected relay. Computer 11 communicates with the sensing subsystem's remote UV sensors 21-24, which provide UV light level readings used by computer 11 to determine when a previously programmed dose of incident UV light has been delivered to each of the remote sensor locations.

The dosage setting is determined by the specific pathogen(s) the operator wants to eradicate. For example, to deliver a disinfection dosage of UV light for the elimination of *Escherichia coli* (*E. coli*) requires 6,600 microwatt-seconds/centimeter-squared for a 100:1 reduction (2 log) in *E. coli*; thus the setting would be 6,600. Existing systems and equipment do not utilize remote sensor(s) for surface and air disinfection therefore they do not offer a way to definitively deliver this dosage to a remote location. The appropriate dosages to provide a particular log reduction in a particular pathogen are well known in the art, and this disclosure is not limited to any particular pathogen, disinfection level, or UV dosage.

Because UV light is harmful to humans, computer 11 communicates with door sensor 30, and if the monitored door has been opened during a disinfection cycle, which may indicate a person has entered the room being treated, the lamps are immediately turned off to prevent injury. The human-computer interface (HCI) may be accomplished via remote control 40, which is used to configure the type and number of sensors to be used for a particular job; to select the minimum dosage of UV light to deliver to each UV sensor; to begin, pause and end a job; and to view job reports stored on computer 11. Pausing the job may be advantageous for various reasons, including the possibility of re-positioning the emitter mid-job in order to obtain fuller coverage of the room. Computer 11 communicates with a remote web server, via the optional internet connected WLAN 50 (if present), to post job reports and status for remote access by password-protected users. The emitter subsystem contains a battery that keeps the computer energized when the subsystem isn't plugged into the facility's electric utility. This battery is automatically recharged as needed from the facility's electric when the subsystem is plugged in. The emitter subsystem also has docks for recharging system sensors that operate by battery power.

Optional components of the present disclosure may be included in order to increase efficacy against particular pathogens. For example, in addition to using UV light, the device may further use a humidity generating device, an ozone generating device, and/or a vaporized hydrogen peroxide gas generating device. The combination of these optional components may provide better and faster disinfection than UV alone.

An integral part of the sterilization system is the sensing subsystem of FIG. 1. The UV light sensing system will measure actual incident light at at least one particular site(s) in an area. An advantage of using incident light over reflected light is that with incident light, sensors can be placed at any site to guarantee that UV radiation reaches a certain minimum dosage at that site. UV sensors 21-24 are designed to measure the total UV light incident upon them. Once all active sensors have received the desired dose, the disinfection procedure is considered complete. One method of measuring total incident UV light is to employ a cosine-corrected sensor, which accounts for all light incident upon it from a full 180 degree solid angle. Another method utilizes multiple sensors, incorporated into a single sensor array, to measure the UV light from various angles of incidence and then to utilize an algorithm to integrate the total light incident upon the sensors to obtain the total incident light from a full 180 degree solid angle. There are other known methods of measuring the total incident UV light upon a sensor, and they are not precluded. For example, the sensors may make one or more instantaneous light measurements (perhaps after waiting for an initial warm-up period), and then calculate total dosage by assuming that the light level remains constant. Unless all the energy is integrated accurately, regardless of the method, it is difficult to determine the actual dosage of UV light delivered. Further, by measuring incident light, the system will not over-radiate an area. This allows for the shortest time for disinfection treatment before re-deployment into another area.

Over-radiating is disadvantageous in the fact that that the rays could cause damage to surfaces in the area unnecessarily. This is in addition to the fact that fewer areas can be finished per unit time. When operating, the UV sensor(s) are designed and programmed to continually measure incident UV light. The intensity measured is converted into a voltage, which is sampled by an analog to digital (A/D) converter, which is part of the UV sensor sub-system. The digital data may then be communicated to central computer 11. In addition to the intensity, a remote sensor may communicate a value representing the charge state of its internal battery. In this way, central computer 11 can be informed ahead of time how much battery life may be left in each remote sensor. One embodiment of this communication is wireless, but wired operation is not precluded. Wireless operation can be accomplished from any number of remote UV sensors back to central computer 11 using one of any number of wireless protocols. An example implementation uses four UV sensors 21-24, but any number is possible. An example wireless protocol is the 802.15.4 Zigbee standard. In addition to wireless UV sensors 21-24, wireless door sensor 30 is included in the network of FIG. 1.

Wireless UV sensors 21-24 may be rechargeable battery operated units. Nonrechargeable or AC-powered units are not precluded. While in operation, the unit may operate completely on battery power. When not in operation, the sensor can be stored in its cradle on the emitter unit, or some other location, at which time re-charging occurs. The set of sensors are operated such that they transmit with different time periods allowing for a lower probability that two units will transmit at the same time. A further embodiment uses buffering of the data at central computer 11 so that if multiple transmissions by sensors occur, the receiver at central computer 11 will not miss any one of them. Another embodiment is for central computer 11 to initiate the request for data from the door and UV sensors on a one-by-one basis thereby eliminating the potential for two units to transmit at the same time. The UV sensors 21-24 are expected to see a relatively constant incident light intensity, and as such, time between transmissions, or the transmission period, can be relatively long. An example transmission period is 10 seconds, but this could range from as short as a few milliseconds to as long as several hours and is easily changed by the operator via the system software.

In the case of a nominal 10 second transmission period, the individual sensors can in one embodiment be programmed to retransmit at a time period equal to a prime number of milliseconds close to 10 seconds or 10,000 milliseconds. For example, sensor 1 might transmit at 9949 milliseconds, sensor 2 at 9967 milliseconds, sensor 3 at 9973 milliseconds and sensor 4 at 10007 milliseconds. These are all prime numbers of milliseconds close to 10 seconds. Setting the transmission period to these time periods greatly reduces the probability of two or more transmissions occurring at the same time. This does not preclude the use of similar time periods amongst UV sensors 21-24 as well.

Central computer 11 may receive the UV sensors' transmissions at the programmed transmission times and then calculate the time difference between receptions of information from each individual sensor in order to integrate the total incident light energy from each sensor and ensure that at least the prescribed dosage has been delivered to each particular sensor location.

This scheme provides another safeguard, because central computer 11 can detect if no messages are being received from a particular sensor for some maximum time from the time the last transmission was received. This condition could occur because of a completely discharged battery or a defect in the sensing unit, in which case operator interaction would be required.

Each system may be equipped with door sensor 30 (or in some embodiments multiple door sensors) for emergency shutoff purposes. Door sensor 30 includes door detector 31 such that if the door opens or closes, central computer 11 will get a notification. If this event occurs while emitter 10 is operating and emitting UV light, then central compute 11 will shut down emitter 10. In addition to door detector 31, door sensor 30 also includes emergency shutoff detector 32, which could be used by an operator to shut down the system even if the door is closed. All of these events are distinguishable by central computer 11 by the message sent to it from door sensor 30. That is, central computer 11 will be able to know which of the above mentioned events occurred because of the digital information transmitted to it.

Latching may be provided on emergency shutoff detector 32. Thus, once emergency shutoff detector 32 is actuated, the indication will remain until reset. The current reset condition occurs when the door is open; however, other methods to reset are possible. Door sensor 30 may also communicate its battery state back to central computer 11 so that the system will know when the battery may need to be recharged and the operator may be notified.

Once the remote sensor(s) and UV emitter are placed where desired, the operator exits the room and begins the activation sequence by placing door sensor 30 in position at the door such that the sensor can detect if the door is opened or closed, or if there is a change from open to closed or vice-versa.

Next, the operator must actuate arming detector 33 located on the door sensor 30. A designed safety feature prevents the system from being armed unless door sensor 30 indicates the door is closed. An open door or a door that is closed when armed and then opened will reset the system to the unarmed state. This design requires the operator to make sure that the door is closed before re-arming emitter 10.

This is of course only one embodiment of a method to arm the system. Another wired or wireless arming detector placed directly on the emitter could also provide a similar function. Under this condition, the door must be open to arm the system. If the door is open, the operator could actuate the arming detector on the emitter. After this detector is actuated and latched (programmed to keep its state as "armed"), the door must close. Once the door is closed, remote control 40 could start the system. If the door has not closed, remote control 40 will not be able to start emitter 10. If the door opened after the emitter started, the emitter would shut down and cease emitting UV light.

Emitter 10 may include one or more additional "drone" emitters. These are additional lights that may be added to the space in order to increase coverage and/or brightness and thereby decrease cleaning time. The drone emitter(s) may be controlled by central computer 11 either by wired or wireless communications.

Door sensor 30 may encode the different switch conditions into a unique voltage measurement. This voltage may be converted to a digital value by an A/D converter, which may be part of door sensor 30 and then sent to central computer 11. The existence of the 3 detectors creates a maximum of 8 different voltage settings. In one embodiment with arming detector 33 as part of door sensor 30, when the door is open, the state of the arming detector is in a "don't care" condition (X). As such, only 6 states need be detected. An example embodiment is shown in Table 1 below, but this does not preclude the use of other techniques to distinguish between the multiple states of door sensor 30.

TABLE 1

An example encoding of the door switch

| Door Position | Arming Switch | Emergency Shutoff Switch | Operation | Voltage (V) | A/D (hex code) |
|---|---|---|---|---|---|
| Closed | Armed | Open | Normal | 1 | AAA |
| Closed | Unarmed | Open | Waiting for Arm | .82 | 8BF |
| Closed | Armed | Closed | Shutdown | 1.39 | ED3 |
| Closed | Unarmed | Closed | Shutdown | 1.21 | CE8 |
| Open | X | Open | Shutdown | 0 | 000 |
| Open | X | Closed | Shutdown | .39 | 428 |

Because door sensor 30 communicates such critical information, its time period of transmission may advantageously be more often than UV sensors 21-24 so that the system can react more quickly to an emergency shutoff event. As such, time periods on the order of 1, typically 0.5 to 1.5, seconds are recommended, but not required. Similarly to UV sensors 21-24, the transmission time could be selected to be a prime number around 1 second to avoid periodic radio frequency (RF) transmissions with the UV sensor group as previously discussed.

Central computer 11 may also be timing the receipt of the messages from door sensor 30. Should central computer 11 not receive a message from door sensor 30 within some maximum time duration, it will shut down the system so that the operator can determine the cause of the loss of door sensor 30 messages. A system malfunction or a discharged battery may be probable causes.

Another system related issue has to do with the identification of UV sensors as opposed to door sensors. Each sensor may have a unique identification number assigned to it. A rule may be used to easily identify the distinction between a UV sensor and a door sensor. An example embodiment would be to use even identification numbers for the door sensors and odd identification numbers for the UV sensors. However, other coding schemes are not precluded. UV sensors and door sensors may be associated with any emitter network under central computer command.

An integral part of the sterilization system is the data logging and reporting performed by central computer 11 as shown in FIG. 1. Data logging provides various capabilities to this system, such as recording door open/close events, recording pause/resume events, recording configuration changes, and providing auditing based upon what user is using the system, what he does, and how effectively rooms are disinfected. Further, electricity usage may be monitored in order to detect lamp or ballast failures.

Upon commencing a disinfection job, a data record is created indicating the location being treated and start time. This record is kept in central computer 11, and a copy is transmitted and posted on a secure web server with access only by authorized users with valid access information including a password. Once the first set of UV sensor readings are received by the computer, the estimated time to completion is calculated by the computer based upon the target dosage and the actual incident intensity measurements. An update is then made to the job data record which includes the latest sensor readings, estimated time to completion, and elapsed time. Other data items including starts and stops, job termination, patient identification numbers, and pathogen being treated for are tracked and reported as well. A unique benefit of this reporting system is the ability for sharing of real-time data among different departments of the facility using the system. In the case of a hospital, the admitting department will benefit from such reporting by having the ability to plan when to send patients to a room based upon the estimated job completion time. Or the cleaning department manager can use the real-time data to locate an employee and track their productivity. The infection prevention department may configure reports to aid in determining the efficacy of their disinfection protocol and to track problem patients or areas of their facility. There are other benefits to real-time access to job data and they are not precluded. An additional feature is the ability to post jobs to be performed to this system via a remote web server. That feature affords interested departments the ability to plan and schedule resources and to plan patient room assignments.

The system employs an Internet Protocol address sharing scheme which enables two or more wireless devices shown in FIG. 1, central computer 11 and remote control 40, the ability to communicate with each other inside or behind a firewall. Typically, the devices acquire an IP address dynamically from the hosting DHCP server so none of the devices can predict the address of any other device. The devices are capable of communicating with the Internet through the firewall, but their local network addresses are translated as their messages are sent out to the Internet. The firewall does not accept incoming traffic except in response to an outbound message.

There is no local name-server in which the devices can store their names and network addresses. The problem becomes a question of how the devices find each other so they can communicate. Within the present disclosure, this may be solved by having central computer 11 capture and send its local untranslated IP address to a remote Internet host. As the message is sent, the address of central computer 11 is translated (encapsulated) by the firewall, but the message payload contains the local untranslated IP address given by the DHCP server inside the firewall. Remote control 40, or another device, contacts the remote Internet host and reads the local untranslated IP address of the computer 11. Remote control 40, or other device, can now directly contact central computer 11 using the local untranslated IP address on the local network inside the firewall. Although the Internet host is outside the firewall and cannot use the untranslated address directly, it can store the address that is scoped to the inside-the-firewall devices. Other inside-the-firewall devices can use the Internet host as name-server for local addresses.

In addition to allowing these devices the ability to communicate with each other, the host facility's firewall automatically blocks all attempts to communicate with them from devices located outside the firewall. All addresses are automatically updated to the remote Internet host any time a new IP address is obtained.

The central computer of the present disclosure may include its own web server, which may be accessed remotely. This allows an authenticated remote user to access local data and even remotely control the system.

In some embodiments, the devices may communicate with the Internet via a wireless telephone network (e.g. a cellular network). This may be advantageous in situations where it is not desirable to rely on the Internet connectivity of the facility.

The Internet connection, in whatever form, is also useful for such purposes as job reporting, remote system configuration, data backup, diagnostics, and remote operation.

Figure 2:
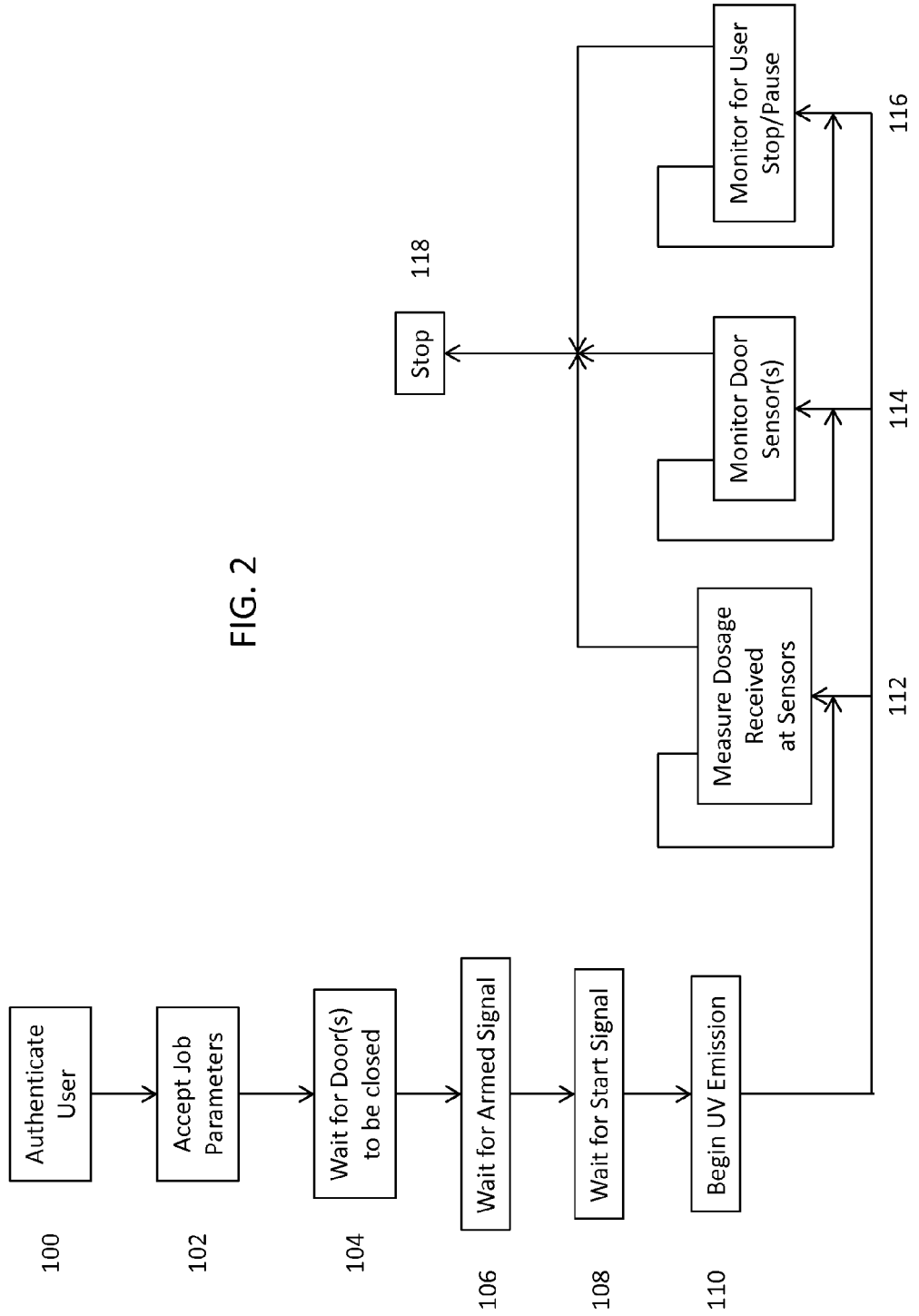
FIG. 2 is a process flow of a method of using the system of the present disclosure.

FIG. 2 presents a flowchart of one embodiment of how a device according to the present disclosure may be operated. At step 100, the user is authenticated via username and password, or any other suitable authentication means, at the remote control (or via an on-site or off-site computer).

At step 102, the user selects various job parameters to configure the system. These parameters may include such items as a name or numerical designator for the room/area being disinfected, a desired UV dosage based on the disinfection level desired and the pathogen(s) to be killed, and what set of peripherals to use in the cleaning. These peripherals include things like the door sensor(s) and UV sensor(s).

At steps 104, 106, and 108 the system waits for the door closed signal(s), armed signal, and start signal to occur, in order. Then at step 110, UV irradiation commences.

While the UV irradiation is in process, the system undergoes three loops: measuring the dosage received at the sensors 112, monitoring the door sensor 114 (which includes the emergency stop button on the door sensor), and monitoring for a user stop/pause instruction 116. When any of these monitoring loops detects its condition, UV irradiation is ceased. The three monitoring loops may advantageously occur at different frequencies. For example, the door monitoring loop is a safety concern, so it may be advantageous for it to occur at a higher frequency than the dosage monitoring loop. The user stop/pause monitoring loop may or may not be implemented as a listening loop; alternatively, it may simply be a command from the user that directly interrupts the UV irradiation. All of these embodiments are within the scope of the present disclosure.

FIGS. 3-11 show screenshots of some of the screens that may be displayed on the remote control of the present disclosure. In the embodiment shown, this software is running on Apple iOS. However, the remote control may provide the same or similar functionality through any of a variety of software platforms.

FIG. 3 shows a Login screen, allowing a user to authenticate via username and password. FIG. 4 shows a Disinfect screen allows the user to select the Unit, the room being cleaned, and the dosage desired. Rooms may be pre-programmed into the system for easy logging and auditing of cleaning procedures and then selected via drop down menus. One embodiment includes automatic position detection, via GPS, inertial positioning, Wi-Fi triangulation, or other suitable methods. The logging of treatment records allows 2D/3D visualizations of things such as untreated areas, areas with high treatment frequency, etc.

FIG. 5 shows the dose and emitter configuration. FIG. 6 shows an About screen, which lists the active sensors and their battery states.

FIG. 7 shows the Disinfect screen, ready to start. At least one UV sensor must be enabled in order for the system to operate.

FIG. 8 shows a Status page listing the parameters of the disinfection job and the estimated time to completion, which the system may calculate based on the UV light levels observed at the UV sensors.

FIG. 9 shows the detail view available in FIG. 8, demonstrating the levels observed at each sensor.

FIG. 10 shows the Status screen of a paused disinfection job, and FIG. 11 shows the option to resume or cancel the paused job. The job may be paused or canceled at any time by the operator via the remote control, so long as there is network connectivity between the remote control and the emitter. If connectivity is lost, the job may be stopped by pressing the emergency stop switch on the door safety sensor. FIG. 12 shows the Status page for a job that has been canceled.

The present disclosure incorporates many other features to ensure safe and reliable operation. Some of them are as follows.

A password-protected remote control, which will only operate the system after a valid user name and password has been entered, prevents unauthorized use of the device.

A fail-safe lamp operating time limit also prevents damage to the lamps and overexposure of the room being treated. The present disclosure includes a built in timer limiting the "on time" for a treatment cycle. This may come initially programmed to limit the maximum lamp "on time" to approximately one hour. It may be changed to any amount of time up to, for example, two hours by an authorized service technician. In the unlikely event of a computer failure, the built in timer will turn off the lamps after the lamps have been on for the programmed amount of time, even if the job hasn't completed.

The present disclosure may also incorporate an internal circuit breaker that will turn off all power to the system in the unlikely event of an overload that is not protected by the facility's circuit protection system. In some embodiments, this may be a 20 amp time delay circuit breaker. This circuit breaker must be manually reset by a qualified technician. To protect against fires and thermal damage, the system may include an internal temperature sensor that will turn off all power in the event the internal temperature of the lower electronics cabinet is at or above the designed temperature limit.

This disclosure may also be equipped with a battery conservation system that automatically turns off power to on-board battery operated devices (including chargers for remote sensors, cooling fan and computer) when it has not been plugged into facility electrical power for a period of time. It is recommended that the device be plugged into facility electrical power when not in use.

The UV emitter may be equipped with two wheels that have push down brakes which, when depressed and locked into place, prevent them from rotating and spinning. The other two wheels are free to rotate and spin. They may be locked such that they can only spin and not rotate, like the rear wheels on a shopping cart.

The foregoing description of illustrative embodiments is provided to enable a person skilled in the art to make and use the disclosed subject matter. Various modifications to these embodiments will be readily apparent to those skilled in the art, and the generic principles defined herein may be applied to other embodiments without the use of the innovative faculty.

The invention claimed is:

1. A tangible computer-readable medium encoding instructions for carrying out a method comprising:
   accepting data to authenticate a user;
   accepting from said authenticated user a set of disinfection job parameters, said set of disinfection job parameters comprising:
   a designator for a room or area to be disinfected;
   a desired UV dosage;
   a set of peripherals to be used in disinfecting said room or area, said set of peripherals comprising at least one safety sensor and at least one UV sensor;
   accepting a door-closed signal from a door sensor coupled to a door adjacent to said room or area to be disinfected;
   accepting an armed signal from said door sensor;
   accepting a start instruction from said authenticated user;
   after accepting said door-closed signal and said armed signal from said door sensor and said start instruction from said authenticated user, initiating emission of UV light from a UV emitter within said room or area to be disinfected;
   monitoring an intensity and a cumulative dose of UV radiation received by said at least one UV sensor;
   ceasing emission of UV light from said UV emitter when said desired UV dosage has been received by all of said at least one UV sensor; and
   indicating a finished state to said authenticated user, said method further comprising ceasing emission of UV light from said UV emitter if said door sensor indicates that said door is open or if communication from said door sensor is interrupted;
   ceasing emission of UV light from said UV emitter if communications from said at least one UV sensor is interrupted; and
   ceasing emission of UV light from said UV emitter if an emergency stop switch is activated on said door sensor.

2. The tangible computer-readable medium of claim 1, wherein said method further comprises the step of: optionally accepting a stop instruction from said authenticated user.

3. The tangible computer-readable medium of claim 1, wherein said method further comprises: optionally accepting a pause instruction from said authenticated user; and optionally accepting a resume instruction from said authenticated user.

4. The tangible computer-readable medium of claim 3, wherein said method further comprises: recording said pause instruction and said resume instruction to allow analysis of protocol and system operation.

5. The tangible computer-readable medium of claim 1, wherein said method further comprises: reading a battery charge state from each of said sensors; notifying said authenticated user if any of said battery charge states is below a predetermined level.

6. The tangible computer-readable medium of claim 1, wherein said method further comprises: communicating with a remote computer for job reporting, remote system configuration, data back-up, diagnostics, or remote operation.

* * * * *